US 11,193,858 B2

(12) United States Patent
Hunter et al.

(10) Patent No.: US 11,193,858 B2
(45) Date of Patent: Dec. 7, 2021

(54) TISSUE PLANING ASSEMBLIES AND METHODS

(71) Applicant: Community Blood Center, Dayton, OH (US)

(72) Inventors: Shawn Aaron Hunter, Springboro, OH (US); Robert Hoskins, Springboro, OH (US); Gregory S. Lucous, Brookville, OH (US)

(73) Assignee: Community Blood Center, Dayton, OH (US)

( * ) Notice: Subject to any disclaimer, the term of this patent is extended or adjusted under 35 U.S.C. 154(b) by 885 days.

(21) Appl. No.: 15/968,311

(22) Filed: May 1, 2018

(65) Prior Publication Data

US 2019/0339169 A1    Nov. 7, 2019

(51) Int. Cl.
*G01N 1/00*    (2006.01)
*G01N 1/06*    (2006.01)

(52) U.S. Cl.
CPC ......... *G01N 1/06* (2013.01); *G01N 2001/063* (2013.01)

(58) Field of Classification Search
None
See application file for complete search history.

(56) References Cited

U.S. PATENT DOCUMENTS

| 2,277,255 A | 3/1942 | Rudert et al. |
| 2,455,831 A | 12/1948 | Townsend |
| 2,522,728 A | 9/1950 | Townsend |
| 2,722,255 A | 11/1955 | Townsend |
| 2,912,027 A | 11/1959 | Townsend |
| 3,519,050 A | 7/1970 | Dobrinen |
| 3,777,599 A | 12/1973 | Reichenbacher et al. |
| 3,898,923 A | 8/1975 | Greider |
| 3,931,665 A | 1/1976 | Townsend |
| 3,949,661 A | 4/1976 | Greider |
| 4,071,923 A | 2/1978 | Smith |

(Continued)

FOREIGN PATENT DOCUMENTS

| CN | 104116549 B | 6/2016 |
| DE | 19958855 A1 | 6/2001 |

(Continued)

OTHER PUBLICATIONS

International Search Report and Written Opinion dated Oct. 30, 2019 for PCT/US2019/029925.

*Primary Examiner* — Jyoti Nagpaul
(74) *Attorney, Agent, or Firm* — Dinsmore & Shohl LLP

(57) ABSTRACT

In one embodiment, a tissue planing assembly includes a base frame, a plurality of disassemblable components assembled to the base frame and having a ready configuration, a sample conveyor, a blade assembly configured to be coupled to the base frame, a control unit communicatively coupled to the sample conveyor, and one or more component sensors communicatively coupled to the control unit. The plurality of disassemblable components is configured to support a tissue sample. The sample conveyor is configured to convey the tissue sample through the blade assembly. The one or more components sensors are configured to output a signal indicative of at least one of the plurality of disassemblable components missing from the ready configuration, wherein the control unit prohibits operation of the sample conveyor when at least one of the plurality of disassemblable components is missing from the ready configuration.

20 Claims, 10 Drawing Sheets

(56) References Cited

U.S. PATENT DOCUMENTS

| | | |
|---|---|---|
| 4,292,710 A | 10/1981 | Townsend |
| 4,606,093 A | 8/1986 | Townsend |
| 4,670,943 A | 6/1987 | Townsend |
| 4,811,459 A | 3/1989 | Townsend |
| 4,996,742 A | 3/1991 | Townsend |
| 5,011,454 A | 4/1991 | Townsend |
| 5,083,973 A | 1/1992 | Townsend |
| 5,122,091 A | 6/1992 | Townsend |
| 5,199,921 A | 4/1993 | Townsend |
| 5,350,334 A | 9/1994 | Holms |
| 5,481,466 A | 1/1996 | Carey |
| 5,558,573 A | 9/1996 | Basile et al. |
| 5,921,980 A | 7/1999 | Kim |
| 5,934,164 A | 8/1999 | Whatley, Jr. |
| 6,066,035 A | 5/2000 | Hergott et al. |
| 6,213,863 B1 | 4/2001 | Basile et al. |
| 6,299,523 B1 | 10/2001 | Wonderlich et al. |
| 6,434,978 B1 | 8/2002 | Mance |
| 6,440,143 B2 | 8/2002 | Kasten |
| 6,553,886 B1 | 4/2003 | Mance |
| 6,589,108 B2 | 7/2003 | Townsend |
| 6,659,856 B2 | 12/2003 | Long |
| 6,698,255 B1 | 3/2004 | Dorstewitz |
| 6,733,530 B1 | 5/2004 | Lam et al. |
| 6,856,852 B1 | 2/2005 | Bruinsma et al. |
| 7,128,642 B1 | 10/2006 | Veldkamp et al. |
| 7,241,213 B2 | 7/2007 | Sawhill et al. |
| 7,338,489 B2 | 3/2008 | Kadoch |
| 7,582,007 B2 | 9/2009 | Sawhill et al. |
| 8,156,853 B2 | 4/2012 | Fujiwara et al. |
| 8,500,523 B1 | 8/2013 | Hart et al. |
| 8,695,782 B2 | 4/2014 | Veldkamp et al. |
| 8,814,881 B2 | 8/2014 | Boles |
| 8,862,262 B2 | 10/2014 | Thorsson et al. |
| 8,892,246 B2 | 11/2014 | Thorsson et al. |
| 9,004,988 B2 | 4/2015 | Van Der Steen et al. |
| 9,027,731 B2 | 5/2015 | Peters et al. |
| 9,055,970 B2 | 6/2015 | Zolotov |
| 9,084,430 B2 | 7/2015 | Maddux et al. |
| 9,089,148 B2 | 7/2015 | Maddux |
| 9,192,172 B2 | 11/2015 | Van Der Steen et al. |
| 9,289,000 B2 | 3/2016 | Thorsson et al. |
| 9,364,010 B2 | 6/2016 | Haines et al. |
| 9,382,025 B2 | 7/2016 | De Vries et al. |
| 9,480,263 B2 | 11/2016 | Van Der Leest et al. |
| 9,594,004 B2 | 3/2017 | Fry et al. |
| 9,687,268 B2 | 6/2017 | Shafirstein et al. |
| 9,993,262 B2 | 6/2018 | Zolotov |
| 10,123,819 B2 | 11/2018 | Mahaffey et al. |
| 2004/0225309 A1 | 11/2004 | Eriksson et al. |
| 2005/0101972 A1 | 5/2005 | Bhatavadekar et al. |
| 2008/0261503 A1 | 10/2008 | Boulanger |
| 2009/0157095 A1 | 6/2009 | Barker et al. |
| 2015/0182241 A1 | 7/2015 | Pratt et al. |
| 2015/0197030 A1 | 7/2015 | Fry et al. |
| 2015/0201954 A1 | 7/2015 | Pratt et al. |
| 2017/0212014 A1 | 7/2017 | Fry et al. |
| 2017/0296173 A1 | 10/2017 | Shelton, IV et al. |
| 2018/0078273 A1 | 3/2018 | Moulton et al. |
| 2018/0333148 A1 | 11/2018 | Gutwein et al. |

FOREIGN PATENT DOCUMENTS

| | | |
|---|---|---|
| DE | 19958855 C2 | 7/2003 |
| DE | 102016120220 A1 | 4/2018 |
| EP | 2600779 B1 | 9/2016 |
| JP | H10286714 A | 10/1998 |
| WO | 2012019094 A2 | 2/2012 |

TISSUE PLANING ASSEMBLIES AND METHODS

TECHNICAL FIELD

The present specification generally relates to tissue planing assemblies and methods and, more specifically, tissue planing assemblies and methods for processing a tissue sample.

BACKGROUND

Skin allografts manufactured from human donor tissue are used for various medical applications. Most notably, allograft skin is used for the purpose of protecting wounds and providing a scaffold for the purpose of promoting new skin cell development and natural healing. Allograft skin consists of both the epidermis and a portion of the dermis of the donor. This is also known as split-thickness (S/T) skin. S/T skin is generally about 0.3 to about 0.65 mm thick and is somewhat difficult to obtain in sections with a surface area larger than 4 in. by 6 in. due to limitations in existing skin recovery methods.

One common method for recovering S/T skin is to use a dermatome or similar bladed instrument to remove the desired thickness directly from the donor. Another method which is commonly used is to remove sections of full-thickness (F/T) skin from the donor to recover S/T skin therefrom. F/T skin consists of the epidermis, dermis and a portion of subcutaneous fat layer and potentially muscle under the dermis. The advantage of recovering F/T skin over the direct recovery method is that the larger sections of skin can then be laid flat and processed to recover the needed S/T skin without the impediment of the donor's anatomical curves and body form. In both cases S/T skin is recovered by processing the tissue epidermis side up.

However, current methods are limited to producing S/T skin graft products with nominal widths of four inches or less based on the width of the blade used to recover the graft. The narrow strips may not be as effective in wound treatment as strips of greater size. Accordingly, a need exists for tissue planing assemblies and methods to produce skin allograft products of greater size than traditional methods.

SUMMARY

In one embodiment, a tissue planing assembly includes a base frame, a plurality of disassemblable components assembled to the base frame and having a ready configuration, a sample conveyor, a blade assembly configured to be coupled to the base frame, a control unit communicatively coupled to the sample conveyor, and one or more component sensors communicatively coupled to the control unit. The plurality of disassemblable components is configured to support a tissue sample. The sample conveyor is configured to convey the tissue sample through the blade assembly. The one or more components sensors are configured to output a signal indicative of at least one of the plurality of disassemblable components missing from the ready configuration, wherein the control unit prohibits operation of the sample conveyor when at least one disassemble component of the plurality of disassemblable components is missing from the ready configuration.

In another embodiment, a tissue planing assembly includes a base frame, a sample conveyor coupled to the base frame, a blade assembly coupled to the base frame, a control unit communicatively coupled to the sample conveyor; and a first hand control and a second hand control communicatively coupled to the control unit. The sample conveyor is configured to convey a tissue sample through the blade assembly. The control unit executes logic to operate the sample conveyer only when both the first hand control and the second hand control are activated.

In yet another embodiment, a method of processing a tissue sample with a tissue planing assembly includes placing a tissue sample epidermis side down on a front tray of the tissue planing assembly, wherein a portion of the tissue sample is contacted to a sample conveyor. The method further includes determining with one or more component sensors whether one or more disassemblable components are assembled to a base frame of the tissue planing assembly in a ready configuration, outputting a ready signal when it is determined that the one or more disassemblable components of the tissue planing assembly are assembled to the base frame of the tissue planing assembly in the ready configuration, and conveying the tissue sample with the sample conveyor through a blade assembly of the tissue planing assembly. The tissue sample is only conveyed when the one or more disassemblable components of the tissue planing assembly are assembled to the base frame in the ready configuration.

In yet another embodiment, a tissue planing assembly includes a base frame, a sample conveyor coupled to the base frame, and a blade assembly coupled to the base frame. The sample conveyor is configured to convey the tissue sample through the blade assembly. The blade assembly includes a shoe defining a groove, a blade positioned on a top surface of the shoe proximate to the groove, a blade clamp configured to rigidly clamp the blade to the shoe, and one or more spacers positionable within the groove adjacent to the blade to adjust a cutting depth of the blade.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Reference will now be made in detail to various embodiments of a tissue planing assembly. In general, tissue planing assemblies as provided herein include a sample conveyor, a control unit communicatively coupled to the sample conveyor and operable to operate the sample conveyor to convey a tissue sample toward a blade assembly such that a tissue planing operation may be performed on the tissue sample. In some embodiments, the tissue planing assembly further includes a plurality of disassemblable components that are assembled to a base frame of the tissue planing assembly in a ready configuration wherein the tissue planing assembly is ready to perform the tissue planing operation. One or more component sensors may be provided that output a signal to the control unit indicative of whether or not one of the one or more disassemblable components are missing from the ready configuration. If a component is missing, the control unit can prohibit operation of the sample conveyor and prevent the planing operation. Such embodiments may aid operators in determining that the tissue planing assembly is ready (i.e., properly assembled) to perform a planing operation. Various embodiments of the tissue planing assembly 100 will be described in more detail herein.

Figure 1:
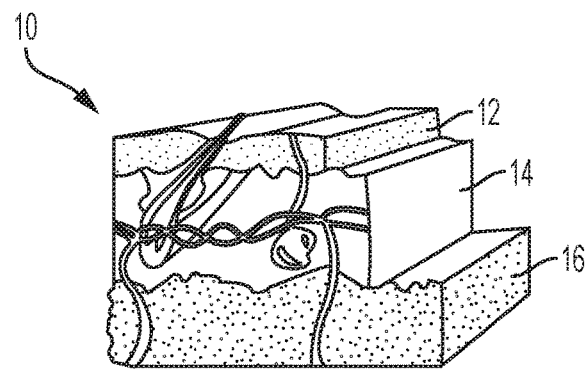
FIG. 1 depicts a tissue sample, according to one or more embodiments shown and described herein.

Referring to FIG. 1, a tissue sample 10 is generally illustrated. The tissue sample 10 is a full thickness (F/T) human skin sample. It is noted that while the present disclosure is directed to planing human skin samples, the embodiments described herein can also apply to non-human tissue samples (e.g., bovine, ovine, suidae, etc.) F/T skin samples generally includes an epidermis layer 12 and a dermis layer 14. Attached to the dermis layer 14 opposite the epidermis layer 12 may be an adipose layer 16 including subcutaneous fat and possibly some muscle tissue. It is noted that where a tissue sample is described as having an epidermis layer 12 and dermis layer 14, the presence of an adipose layer 16 is not precluded.

F/T skin samples are typically removed from a donor's back, upper and lower extremities, and occasionally abdomen in large sections via sharp dissection with a scalpel and/or other tissue cutting devices. The advantage of recovering F/T skin is that large sections of skin can be removed from the donor, laid flat, and processed without the impediment of the donor's anatomical curves and body form. Using the methodologies provided herein, large F/T skin samples may translate into larger pieces of split thickness (S/T) skin samples with a more consistent thickness than presently available using traditional S/T skin recovering techniques.

S/T skin includes the epidermis layer 12 and a portion of the dermis layer 14. S/T skin can be used as skin grafts to better aid healing in patients. S/T skin is generally between about 0.3 and about 0.65 mm thick (e.g., 0.45 mm thick). One drawback of beginning with F/T skin is that it may be difficult to hold the tissue sample 10 firmly in place throughout a tissue planing operation to recover the S/T skin. Under traditional processing techniques, a technician may need to hold the F/T skin sample with their hands while simultaneously using a cutting device to obtain the S/T skin.

As noted above, under traditional S/T skin recovering techniques, cutting devices (e.g. dermatomes, amalgatomes, and the like) are used to directly remove the desired S/T skin from the F/T skin sample. That is, the F/T skin sample is processed epidermis side up and a cutting device is applied directly to the epidermis from above by an operator to remove the S/T skin. Conventional S/T skin grafts recovering techniques therefore limit the resulting S/T graft size to the cutting width of the cutting device, which is generally about 6 inches wide or less. These cutting devices are applied manually by an operator and, therefore, need to be sized so as to be controllable and easy to control within the hand of an operator. However, wider S/T skin grafts are desirable to better meet demands of patients with larger wounds. As will be described in greater detail herein, using the tissue planing assemblies and methods described herein allow for processing the tissue sample 10 epidermis side down with a much wider blade assembly resulting in larger width S/T skin grafts.

Figure 2A:
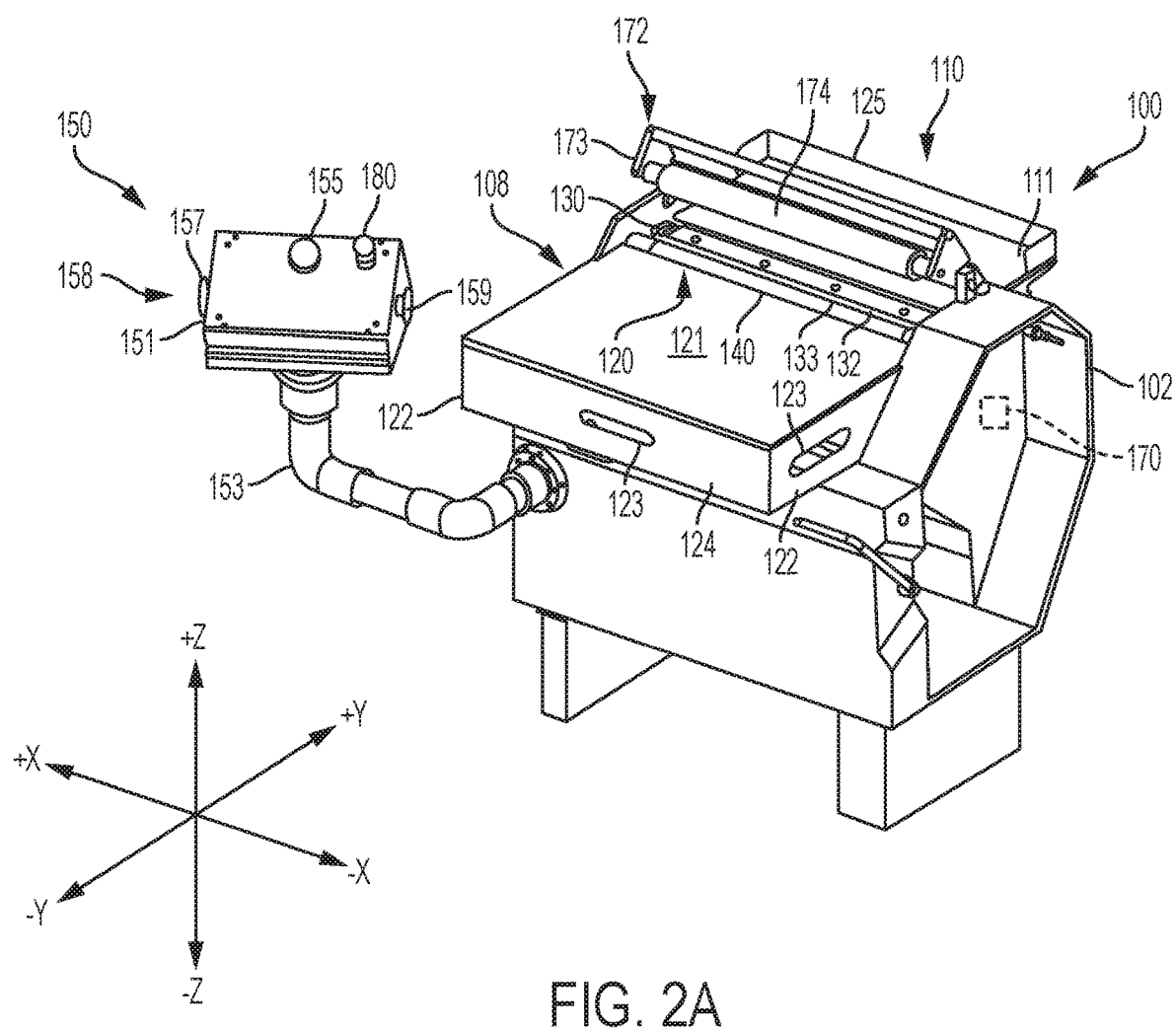
FIG. 2A depicts a front perspective view of a tissue planing assembly, according to one or more embodiments shown and described herein.
Figure 2B:
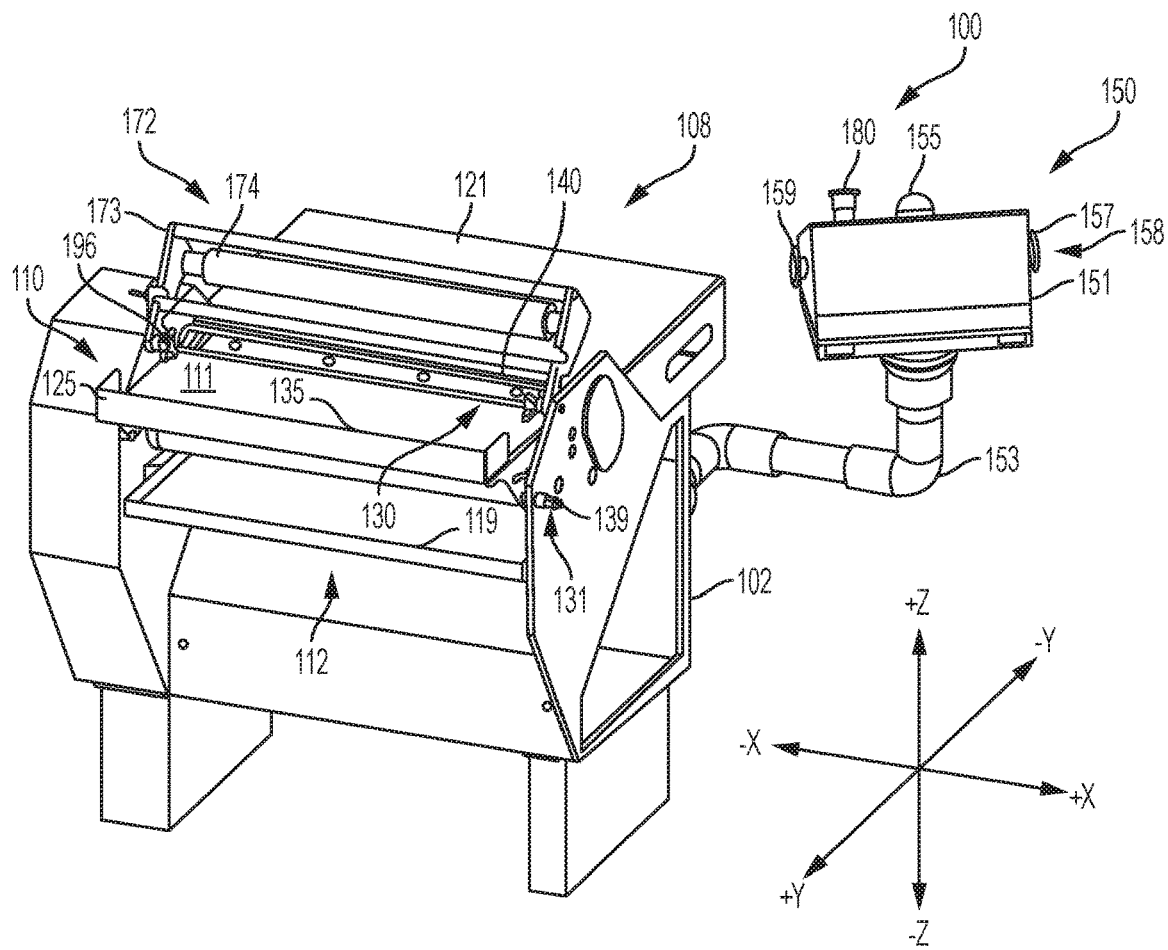
FIG. 2B depicts a rear perspective view of the tissue planing assembly of FIG. 2A, according to one or more embodiments shown and described herein.

Referring to FIGS. 2A and 2B, a front perspective view and a rear perspective view of the tissue planing assembly 100 is respectively illustrated. The tissue planing assembly 100 includes a base frame 102, a sample conveyor 120, a blade assembly 130, a plurality of removable trays including a front tray 108, a rear tray 110, and a catch tray 112, and a rotatable hold down roller 172. The tissue planing assembly 100 may further include one or more component sensors 170, a control unit 150, a control unit housing 151, a status indicator 155, a user input module 158, and an emergency stop 180. While these various components are illustrated as part of a single tissue planing assembly, tissue planing assemblies having a greater or fewer number of components are possible and contemplated.

The base frame 102 supports the various components of the tissue planing assembly 100 relative to one another such that a tissue planing operation may be performed. It is noted that the base frame 102 may be made from any material that can be repetitively washed and disinfected (e.g., stainless steel). In some embodiments, the base frame 102 may be electro-polished or provided with a similar high durability and mirrored surface treatment such that the base frame 102 may be easily cleaned and sterilized.

Figure 3A:
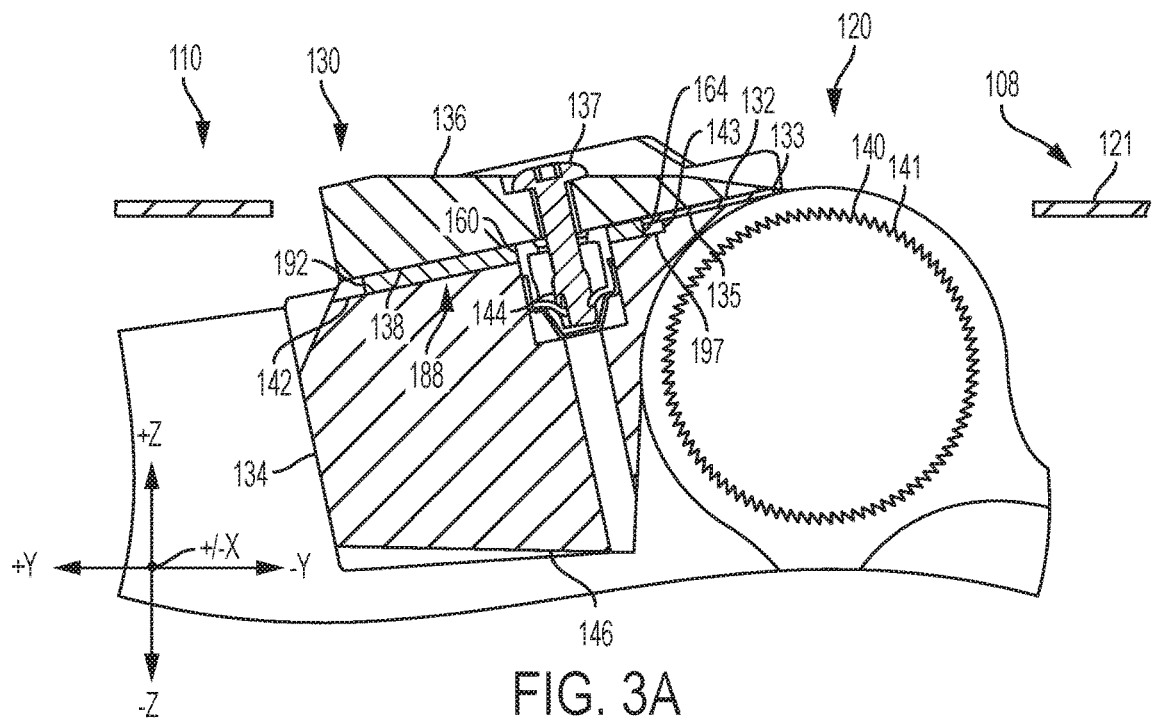
FIG. 3A illustrates a cross section of the tissue planing assembly of FIG. 2A transverse to a sample conveyor having a first blade position, according to one or more embodiments shown and described herein.
Figure 3B:
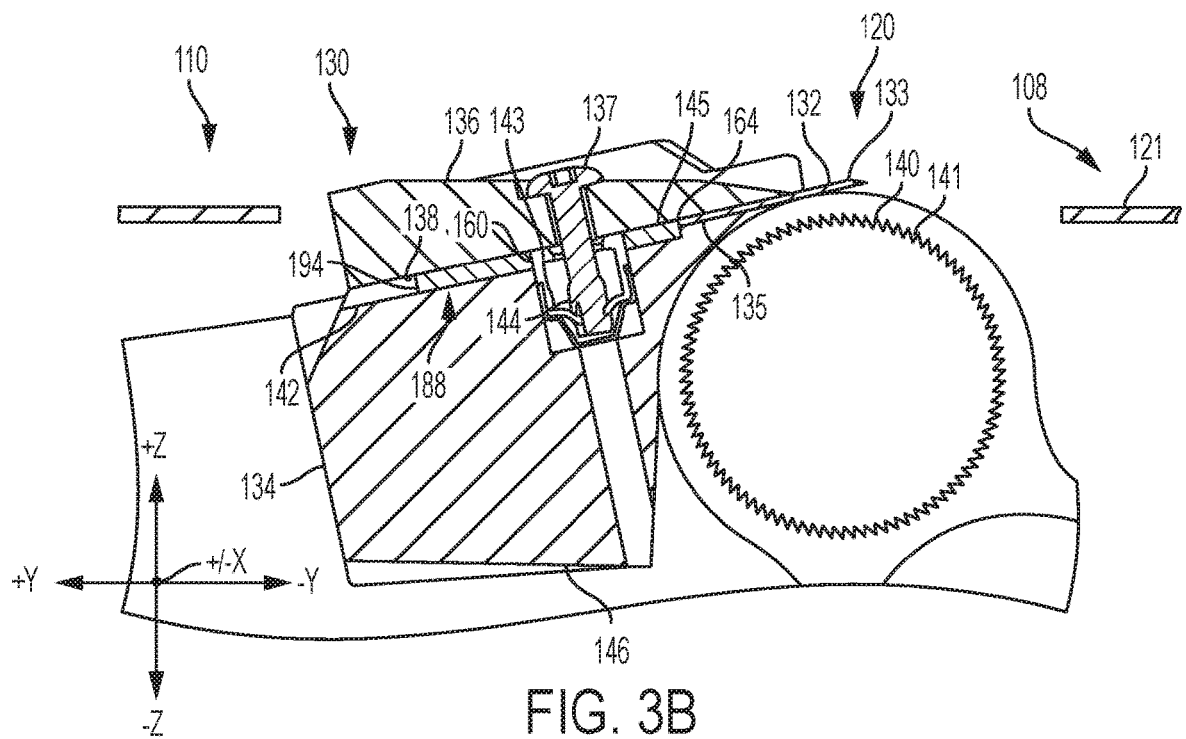
FIG. 3B illustrates the cross section of the tissue planing assembly of FIG. 3A with a second blade position, according to one or more embodiments shown and described herein.

Still referring to FIGS. 2A and 2B, mounted to the base frame 102 is a sample conveyor 120. The sample conveyor 120 may be any device configured to pull a tissue sample from a sample support surface 121 of the front tray 108 and through the blade assembly 130 such that a tissue planing operation can be performed on a tissue sample. FIGS. 3A and 3B illustrate a cross section of the tissue planing assembly 100 transverse to the sample conveyor 120. In the illustrated embodiment, the sample conveyor 120 includes a gripping roller 140 having a plurality of teeth 141 extending from a peripheral surface of the gripping roller 140. The plurality of teeth 141 of the gripping roller 140 allows the sample conveyor 120 to interact with a tissue sample so as to be able to propel the tissue sample toward the blade assembly 130 (see also FIG. 11B). The sample conveyor 120 may include a motor, not shown, to rotatively drive the gripping roller 140. In some embodiments, and as will be described in greater detail herein, the control unit 150 can be communicatively coupled to the sample conveyor 120, and execute logic to selectively operate or disable operation of the sample conveyor 120.

Figure 11A:
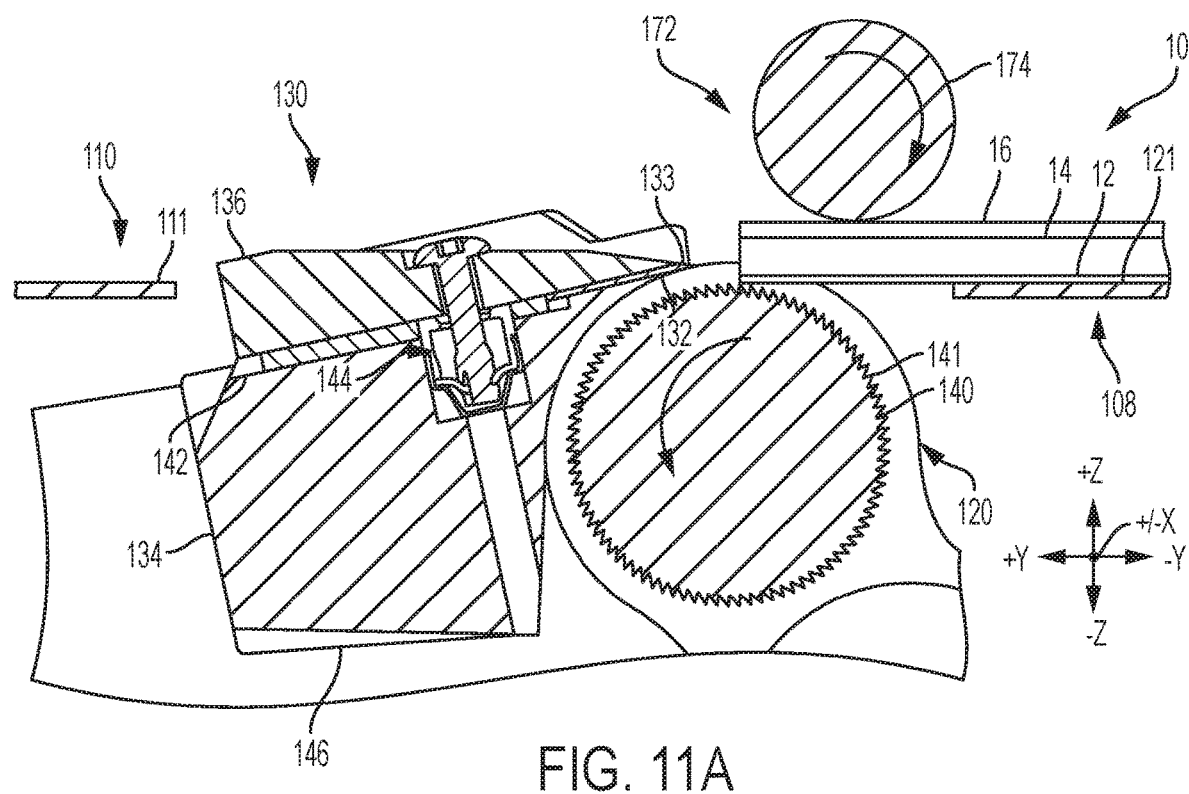
FIG. 11A illustrates a tissue sample prepared for processing, according to one or more embodiments shown and described herein.
Figure 11B:
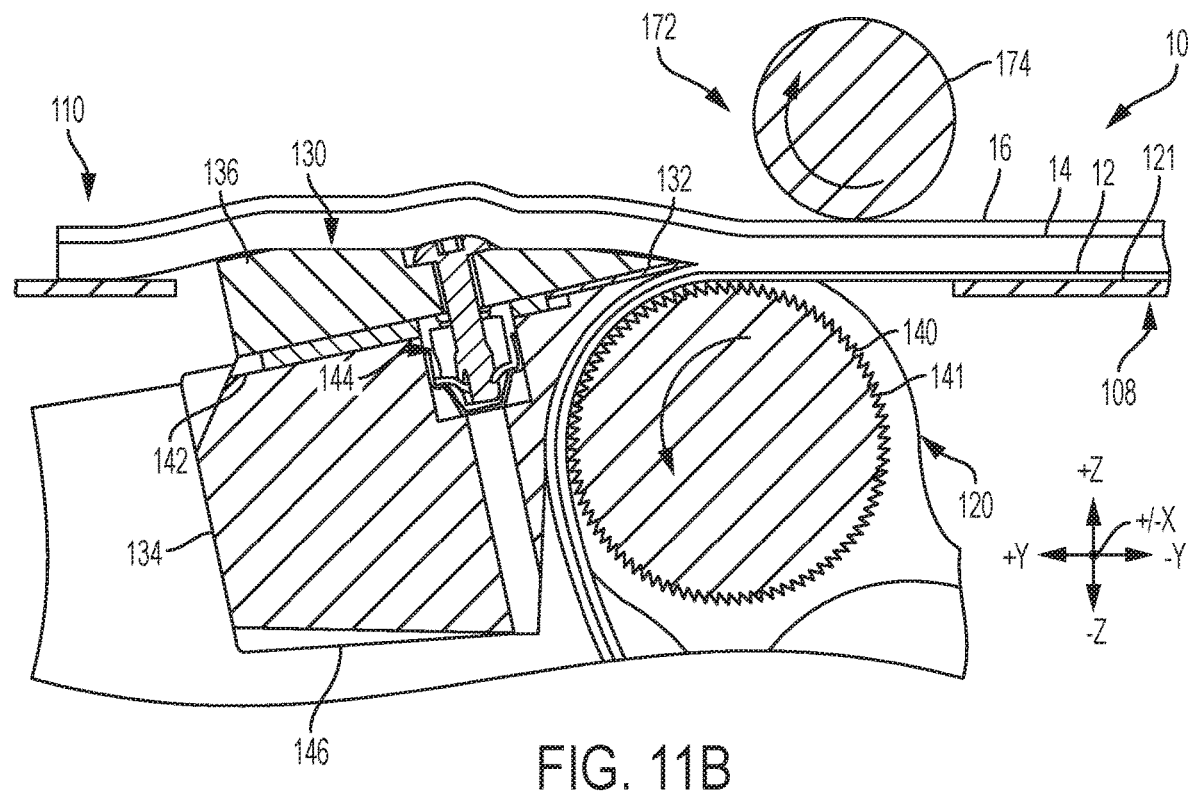
FIG. 11B illustrates the tissue sample of FIG. 11B being processed, according to one or more embodiments shown and described herein.

As best seen in FIGS. 2A-3B, the blade assembly 130 is positioned closely adjacent to the gripping roller 140 of the sample conveyor 120 so as to be able to plane a tissue sample as a tissue sample is directed into the blade assembly 130 by the gripping roller 140 (see also FIG. 11B). The blade assembly 130 includes an elongated cutting blade 132 mounted on a shoe 134 by a blade clamp 136. The blade 132 further has a cutting edge 133 that extends beyond the shoe 134 and the blade clamp 136 so as to be exposed and capable of performing a tissue planing operation.

Referring specifically to FIG. 3A, the shoe 134 has a top surface 135 and a groove 142 formed within the top surface 135 of the shoe 134. The cutting blade 132 may sit on the top surface 135 of the shoe such that the cutting edge 133 extends beyond the shoe 134. A portion of the cutting blade 132 may extend over the groove 142. Positioned within of the groove 142, in the longitudinal (+Y) direction may be an aperture 144 for receiving a fastener 137 from the blade clamp 136. The aperture 144 may extend through a bottom surface 146 of the shoe 134 to provide for drainage of fluids (e.g., saline) used to aid in the performance of a tissue planing operation on a tissue sample.

The blade clamp 136 includes a substantially planar clamping surface 138 that is directed to the top surface 135 and groove 142 of the shoe 134. The blade clamp 136 may include a fastener 137 for releasably fastening the clamp and the shoe 134 together so as to clamp the cutting blade 132 therebetween.

In some embodiments, the position of the blade 132 in the longitudinal direction (+/−Y) may be adjusted such that a greater or lesser amount of the cutting blade 132 is exposed beyond the shoe 134 and the blade clamp 136, which adjusts a cutting depth of the blade 132. In some embodiments, a spacer 188 may be positioned within the groove 142 of the shoe 134 behind the blade 132 and clamped into place by the blade clamp 136 to allow the blade 132 to shift in the +Z/−Y quadrant. As noted above, this blade translation may allow for adjustment of a thickness of a finished skin graft while maintaining a uniform and consistent output.

FIG. 3A illustrates a first spacer 192 corresponding to a first cutting depth. In the illustrated embodiment the first spacer 192 includes an opening 160 formed therein to allow the fastener 137 to pass therethrough to clamp the first spacer 192 into place. In this embodiment, the first spacer 192 is positioned such that there is a gap 197 formed between the first spacer 192 and an end 143 of the groove 142. The cutting blade 132 may bridge this gap 197 to contact a leading edge 164 of the first spacer 192 such that the blade 132 is unable to travel further in the +Y direction of the depicted coordinate axes.

FIG. 3B illustrates a second spacer 194 corresponding to a second cutting depth. In this embodiment, the second spacer 194 includes an opening 160 formed therein to allow the fastener 137 to pass therethrough to clamp the second spacer 194 into place. In this case, the second spacer 194 extends to the end 143 of the groove 142. The cutting blade 132 is positioned so as to be in contact with the leading edge 164 of the second spacer 194. In this case, the second spacer 194 causes the cutting edge 133 of the cutting blade 132 to extend further in the −Y direction of the depicted coordinate axes than the position of the cutting edge 133 illustrated in FIG. 3A.

Figure 4A:
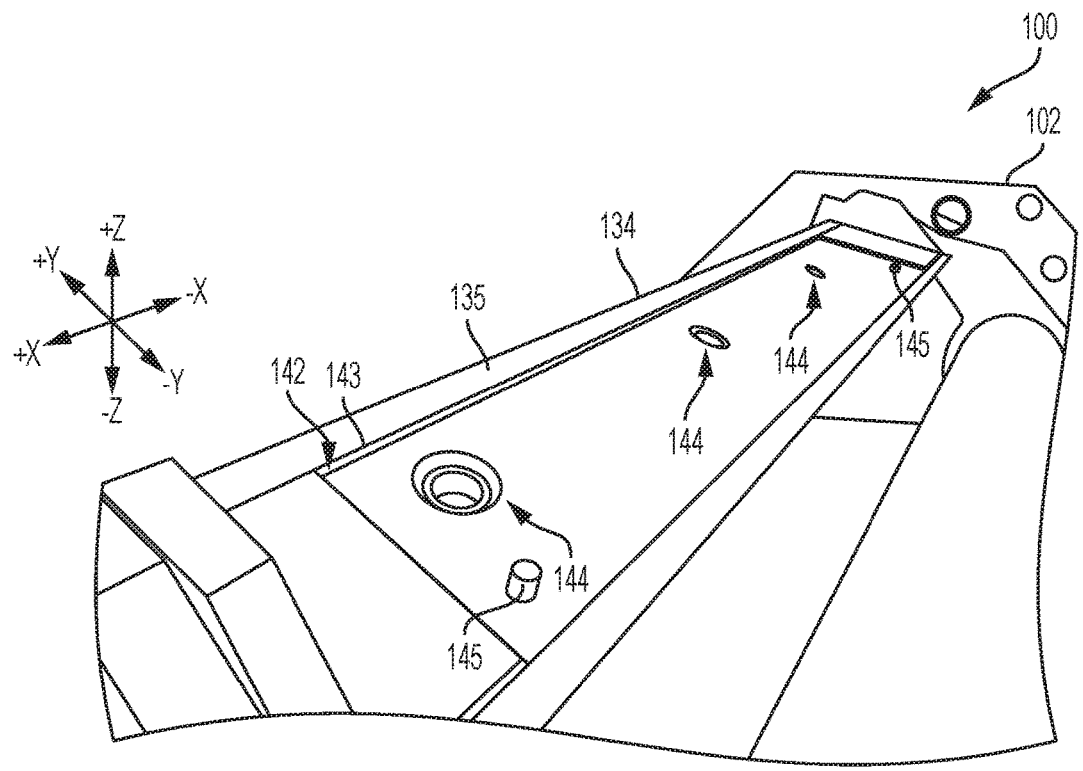
FIG. 4A illustrates a perspective view of a shoe of the tissue planing assembly of FIG. 2A, according to one or more embodiments shown and described herein.
Figure 4B:
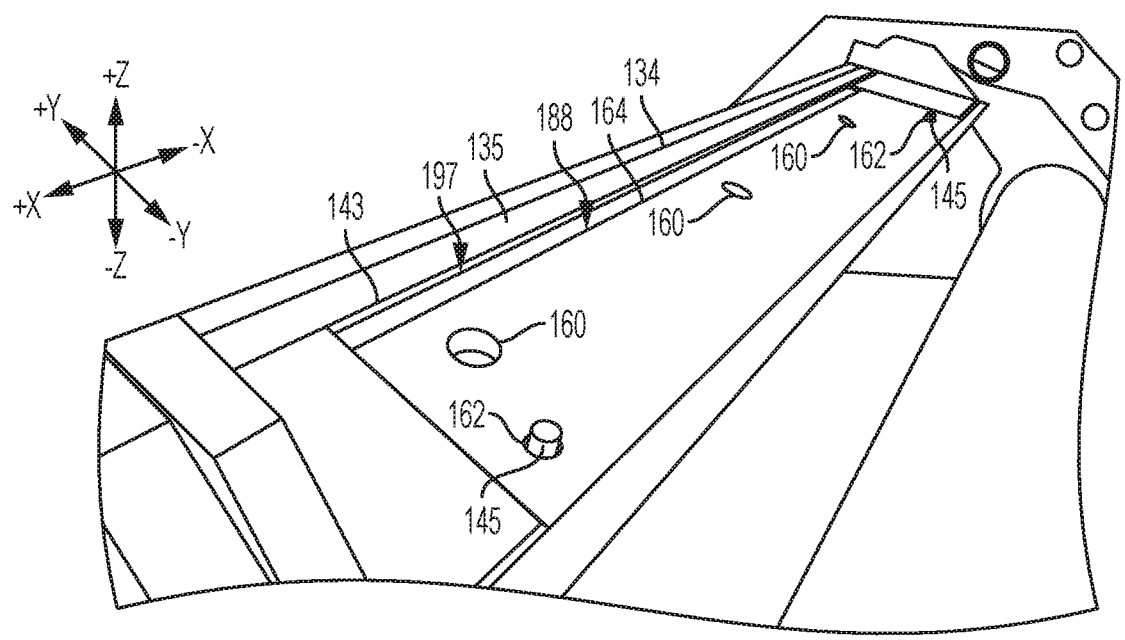
FIG. 4B illustrates a perspective view of the shoe of FIG. 4A with a spacer positioned within a groove of the shoe, according to one or more embodiments shown and described herein.
Figure 4C:
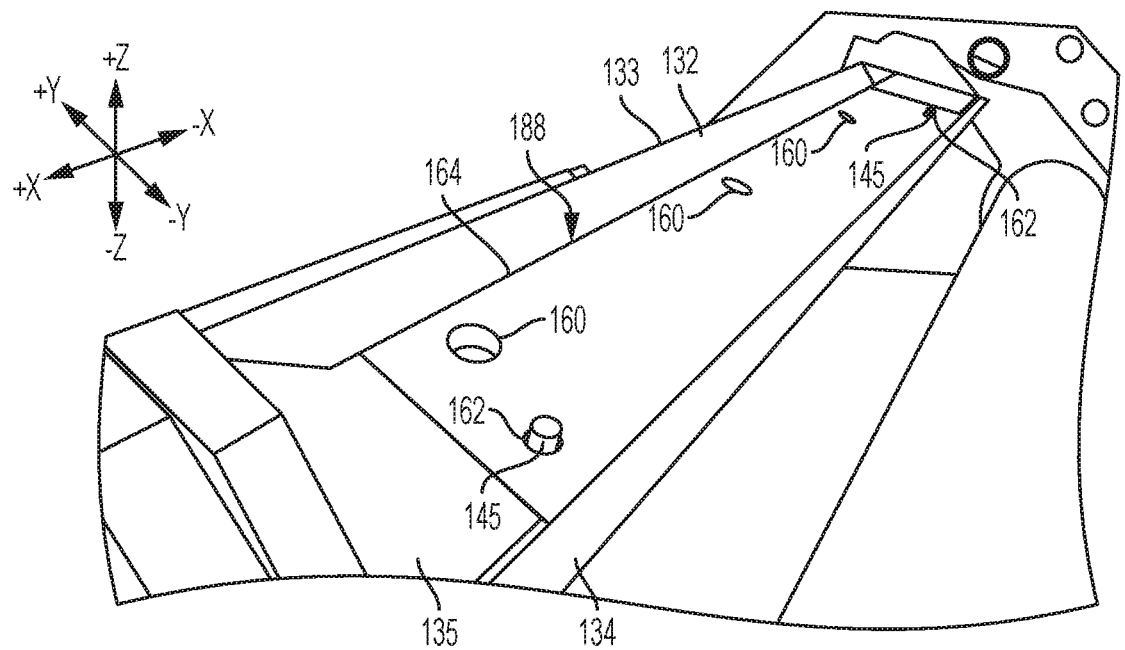
FIG. 4C illustrates the shoe of FIG. 4B with a cutting blade positioned on a top surface of the shoe, according to one or more embodiments shown and described herein.

Referring now to FIGS. 4A-4C, FIG. 4A illustrates a perspective view of an embodiment of the shoe 134 without a blade clamp, spacer, or blade. As shown the groove 142 extends along a length of the blade clamp in the −X direction of the depicted coordinate axes. Positioned within the groove 142 are several apertures 144 for receiving a fastener for the blade clamp 136 (shown in FIGS. 3A and 3B). Though, three apertures 144 are illustrated a greater or fewer number of apertures 144 are contemplated and possible. In some embodiments, one or more dowel rods 145 may extend from the groove 142 which may be used to position a spacer within the groove 142.

FIG. 4B illustrates a spacer 188 positioned within the groove 142. The spacer 188 may include as many openings 160 to match the number of apertures within the shoe 134. As shown, the one or more dowel rods 145 of the shoe 134 may extend through dowel rod openings 162 formed within the spacer 188 to position the spacer 188 relative to the end 143 of the groove 142. FIG. 4C illustrates the blade 132 positioned on the top surface 135 of the shoe 134 and contacting a leading edge 164 of the spacer 188. Accordingly, the spacer 188 extends above the top surface 135 of the shoe 134 to be flush with a top surface of the cutting blade 132.

One or more spacers may be provided. In some embodiments, several spacers may be provided to allow to standardized cutting depths to be chosen for a particular product. The several spacers may generally have the same dimensions, but are positioned within the groove 142 so as to extend closer or farther from the end 143 of the groove 142. Accordingly, the positioning of the openings 160 for the fastener and/or the dowel rod openings 162 within the spacer 188 may vary between different spacers. For example, a spacer 188 that has a leading edge 164 that is to be positioned closer to the end 143 of the groove 142 (see FIG. 3B) may have the opening 160 formed therein positioned farther back in the +Y direction of the depicted coordinate axes than that of a spacer 188 having a leading edge 164 that is to be positioned farther from the end 143 of the groove 142 (see FIG. 3A).

It is noted that when assembled, the blade 132 is held rigidly in place by the shoe 134, the clamp 136, and the spacer 188 with respect to the base frame 102. That is, a cutting depth of the blade 132 is configured to remain constant throughout processing such that a S/T skin graft having a substantially uniform thickness can be reliably and repeatedly achieved.

In some embodiments, at least some of the various components can be easily assembled and disassembled to and from the base frame 102. Accordingly, the various components that are easily assembled and disassembled to and from the base frame 102 define a plurality of disassemblable components. Generally, the plurality of disassemblable components may be assembled to or disassembled from the base frame 102 without the need of separate tools. For example the plurality of disassemblable components may mount onto the base frame 102 using slots, pins (e.g., spring loaded pins), and the like. The plurality of disassemblable components may include, without limitation, one or more of the plurality of removable trays (e.g., the front tray 108, the rear tray 110 and/or the catch tray 112), and the rotatable hold down roller 172. However, other components may also be included as one of the plurality of disassemblable components without departing from the scope of the present disclosure.

The plurality of disassemblable components may be assembled to the base frame 102 in a ready configuration, such as illustrated in FIGS. 2A and 2B, wherein the plurality of disassemblable components are mounted on to the base frame 102, such that the tissue planing assembly 100 is ready to perform a tissue planing operation. As noted above, the tissue planing assembly 100 may include one or more component sensors 170 that are configured to output a signal indicative of at least one of the plurality of disassemblable components missing from the ready configuration. As will be described in greater detail herein, when at least one of the plurality of disassemblable components is missing from the ready configuration, by either being out of alignment or missing completely from the tissue planing assembly 100, the control unit 150 can execute logic to prohibit operation of the sample conveyor 120.

Still referring to FIGS. 2A, and 2B, removably supported on the base frame 102 is the front tray 108. In some embodiments, the front tray 108 may be electro-polished or provided with a similar high durability and mirrored surface treatment such that the front tray 108 may be easily cleaned and sterilized. Alternatively, or in addition to such treatment, the front tray 108 may be made from a material capable of repeated washing and sterilization (e.g., stainless steel). Referring also to FIG. 11A, the front tray 108 may be used to support a tissue sample 10 thereon as the tissue sample 10 is introduced to blade assembly 130 and throughout processing. The front tray 108 includes a sample support surface 121 for supporting the tissue sample 10 thereon and one or more sidewalls that extend from the support surface. For example, in the illustrated embodiment, the front tray 108 includes a longitudinal side wall 124 and two lateral side walls 122 that are perpendicular to the longitudinal sidewall 124. The side walls may extend perpendicularly from the sample support surface 121 in the vertical direction (−Z) and may define hand holds 123 formed therein. The hand holds 123 may allow a user to manually manipulate the front tray 108 such that the front tray 108 may be easily assembled and disassembled to the base frame 102. The front tray 108 may be light enough for a single user to manipulate. For example, in some embodiments the front tray weights less than 25 pounds (e.g., 23 lbs).

The front tray 108 may be mounted to the base frame 102 using any means that does not require tools to assemble or disassemble the front tray 108 to or from the base frame 102. For example the front tray 108 may be mounted on to the base frame 102 using, pins, slots, or a combination thereof. Accordingly, the front tray 108 may be one of the disassemblable components of the plurality of disassemblable components.

Figure 5:
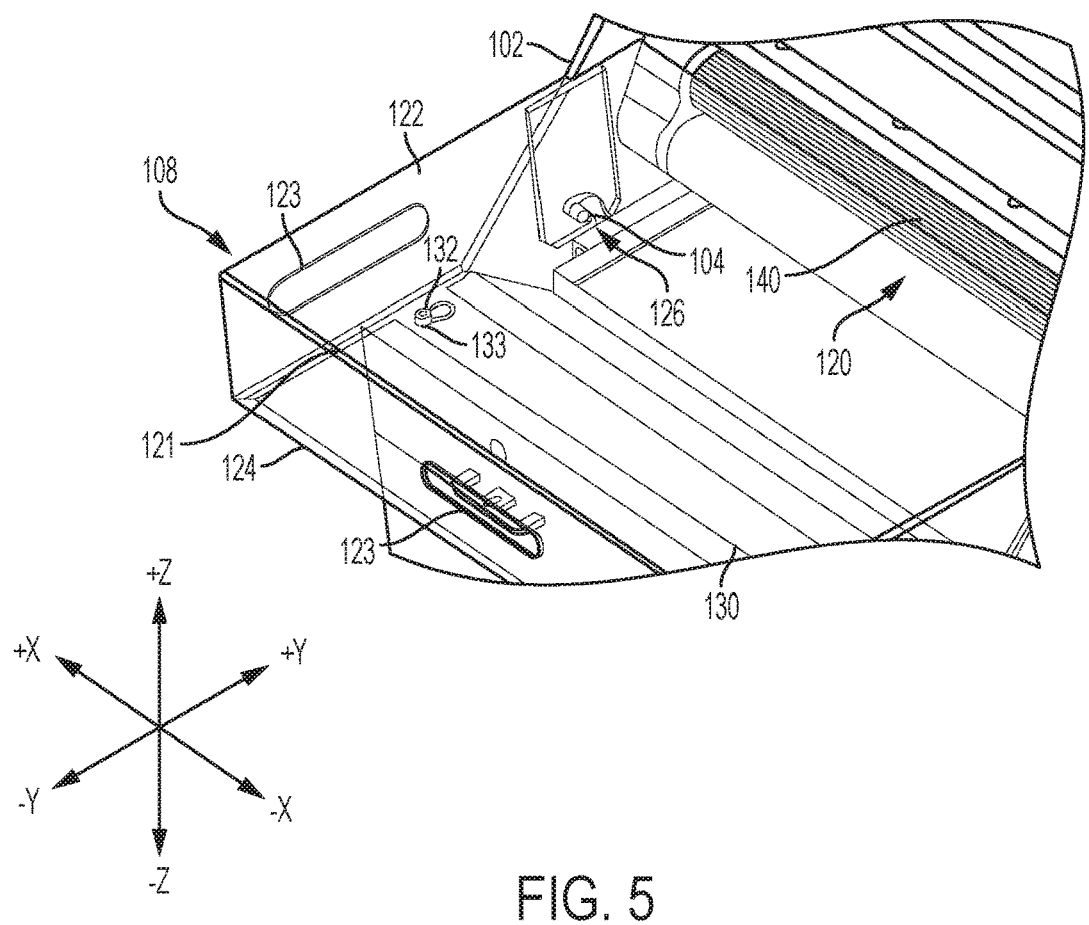
FIG. 5 depicts a connection between a front tray and a base frame of the tissue planing assembly of FIG. 2A, according to one or more embodiments shown and described herein.

For example, FIG. 5 illustrates a perspective view of a connection between the front tray 108 and the base frame 102. The front tray 108 is illustrated in ghost such that the connection between the front tray 108 and the base frame 102 is more easily viewed. In such embodiments, the front tray 108 has a receiver slot 126 formed within the lateral side wall. In the present embodiment, the receiver slot 126 may extend substantially vertically through the lateral side wall and then veer from the vertical orientation to a substantially horizontal orientation. The base frame 102 may define a pin 104 insertable into the receiver slot 126 of the front tray 108. Accordingly, when front tray 108 is positioned on the base frame 102, the pin 104 may traverse the substantially vertical portion of the slot 126 and the tray may be push forward in the +Y direction, as indicated in the depicted coordinate axes, such that the pin 104 sits within the substantially horizontal portion, when the front tray 108 is positioned in the ready configuration. This may prevent unwanted movement of the front tray 108 in the vertical direction once the pin 104 is within the substantially horizontal portion of the receiver slot 126. In some embodiments, to prevent the front tray 108 from rotating about an axis defined by the pin 104, the front tray 108 may include a bottom securing strip 130 with a second slot 132 formed therein. The second slot 132 may include a widened portion and a narrow portion wherein a second pin 133 extending from the base frame 102 can be inserted in to the wider portion, but when the front tray 108 is pushed forward to the ready configuration, the narrower portion locks in around the neck of the second pin 133, such that the front tray 108 cannot be lifted in the vertical direction. It is noted that while the slot and pin connections between the front tray 108 and the base frame 102 are illustrated on one side of the front tray 108, similar or identical slot and pin connections may be present on the opposite side of the front tray 108.

Referring again to FIGS. 2A and 2B, the rear tray 110 is configured to be positioned at a distal end (i.e., rearward) of the blade assembly 130 and is configured to receive a portion of a tissue sample as the tissue sample is conveyed through the blade assembly 130 by the sample conveyor 120. Stated another way, as a tissue sample 10 is passed through the blade assembly 130, a first portion of the tissue sample 10 is directed between the shoe 134 and the gripping roller 140 and a remainder portion of the tissue sample is directed over the blade clamp 136 toward the rear tray 110 (see also FIG. 11B). The rear tray 110 accordingly supports the remainder portion of the tissue sample that passes over the blade clamp 136 on a tissue support surface 111. Surrounding a portion of the tissue support surface 111 may be lip 125 extending from the tissue support surface 111, which is configured to retain the tissue sample 10 thereon. Accordingly, the portion of the tissue sample that is directed onto the rear tray 110 can be retained on the rear tray 110 instead of potentially falling off an end of the tissue support surface 111. In some embodiments, the rear tray 110 may be electro-polished or provided with a similar high durability and mirrored surface treatment such that the rear tray 110 may be easily cleaned and sterilized. Alternatively, or in addition to such treatment, the rear tray 110 may be made from a material capable of repeated washing and sterilization (e.g., stainless steel).

Moreover, the rear tray 110 may be lightweight for a user to easily manipulate, for example the rear tray 110 may weigh less than 10 lbs.

Figure 6A:
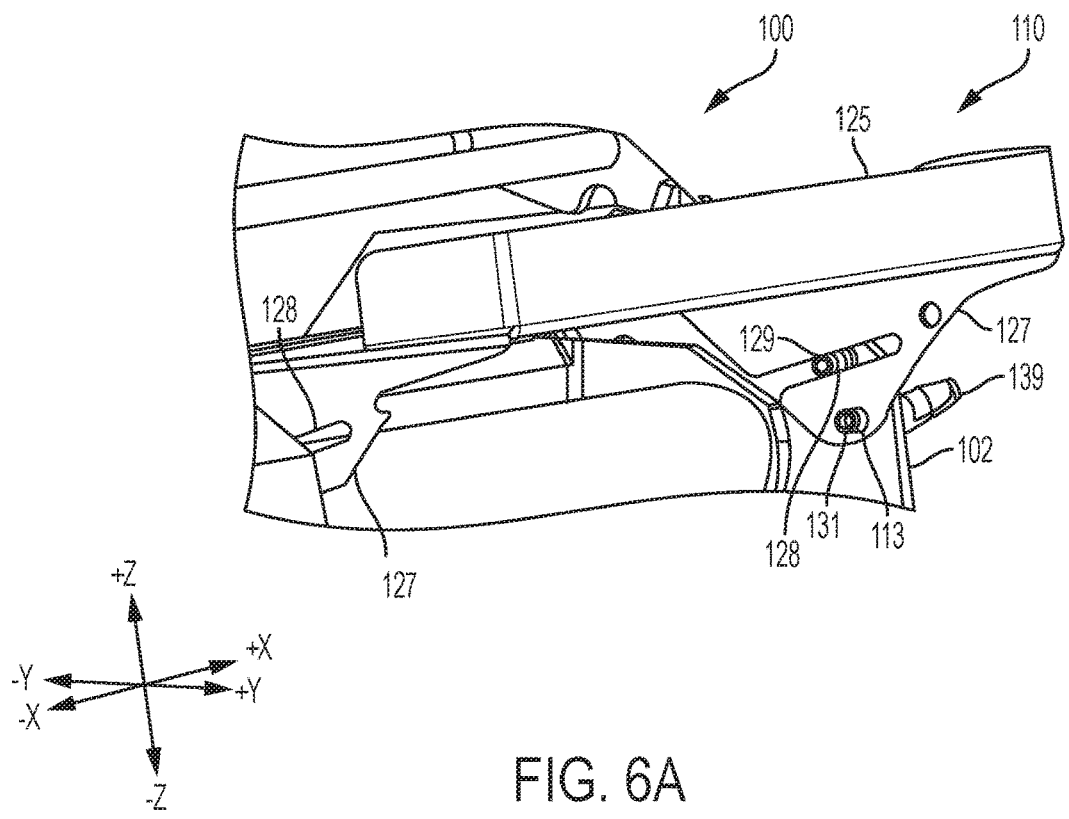
FIG. 6A illustrates a perspective view of a rear tray mounted on to the base frame of the tissue planing assembly of FIG. 2B, according to one or more embodiments shown and described herein.

FIG. 6A illustrates a perspective view of the rear tray 110 mounted on to the base frame 102. As noted herein, the rear tray 110 may be one of the disassemblable components of the plurality of disassemblable components. In particular, FIG. 6A illustrates a connection between the rear tray 110 and the base frame 102. In this case, the rear tray 110 includes side walls 127 that have a slot 128 formed therein. A rear tray pin 129 projecting from the base frame 102 is insertable into the slot 128 to properly mount the rear tray 110 on to the base frame 102. The base frame 102 may also include locking pin 131 coupled to a handle 139 that can extend through an aperture 113 formed within the side wall 127 of the rear tray 110 to lock the rear tray 110 into place, in the ready configuration. The handle 139 may allow easy inserting and/or removing of the locking pin 131 to and from engagement with the rear tray 110. In some embodiments, the locking pin 131 may be spring loaded and biased to the locked position.

Figure 6B:
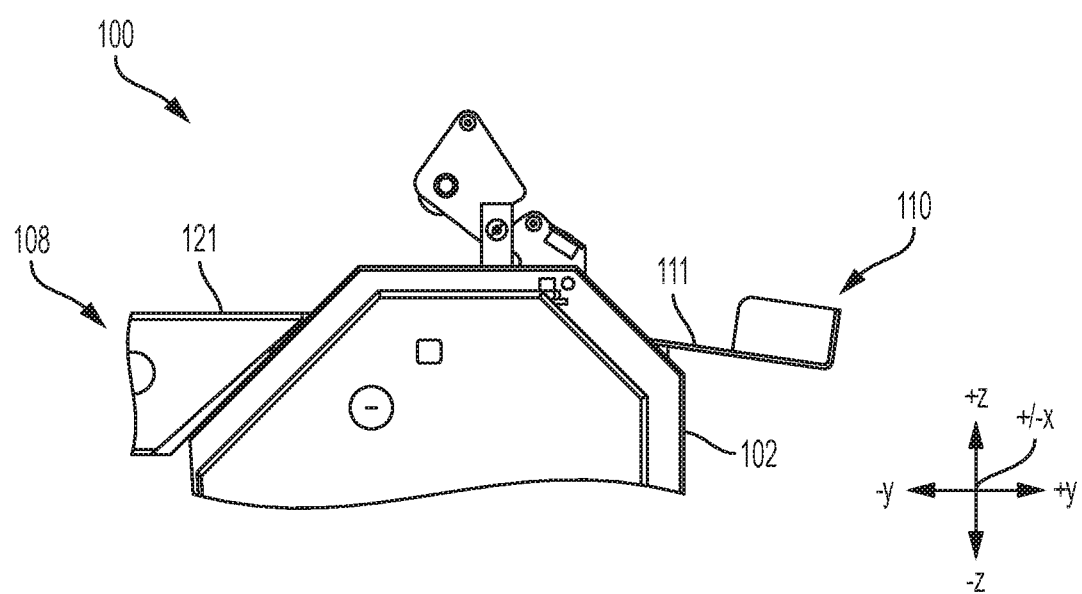
FIG. 6B illustrates a side view of an alternative orientation of the rear tray mounted on to the base frame of the issue planing assembly, according to one or more embodiments shown and described herein.

Referring now to FIG. 6B, the rear tray 110 is illustrated with an alternative orientation as compared to FIG. 6A. As illustrated, in some embodiments, the rear tray 110 may be angled (i.e., oriented at a non-zero angle) relative to the front tray 108. Stated another way, the tissue support surface 111 may be angled relative to the sample support surface 121 of the front tray 108. In particular, the tissue support surface 111 may be angled downward in the −Y/−Z quadrant as indicative by the illustrated coordinate axes. By angling the tissue support surface 111 of the rear tray 110 downward, gravity may aid in propelling a tissue sample through the blade assembly 130. In yet further embodiments, the rear tray 110 may be rotatably adjusted about an axis defined by a connection between the base frame 102 and the rear tray 110 to achieve various degrees of the rotation. Accordingly, the tissue support surface 111 of the rear tray 110 may be rotatably adjustable with respect to the sample support surface 121 of the front tray 108 to various angles.

Figure 7:
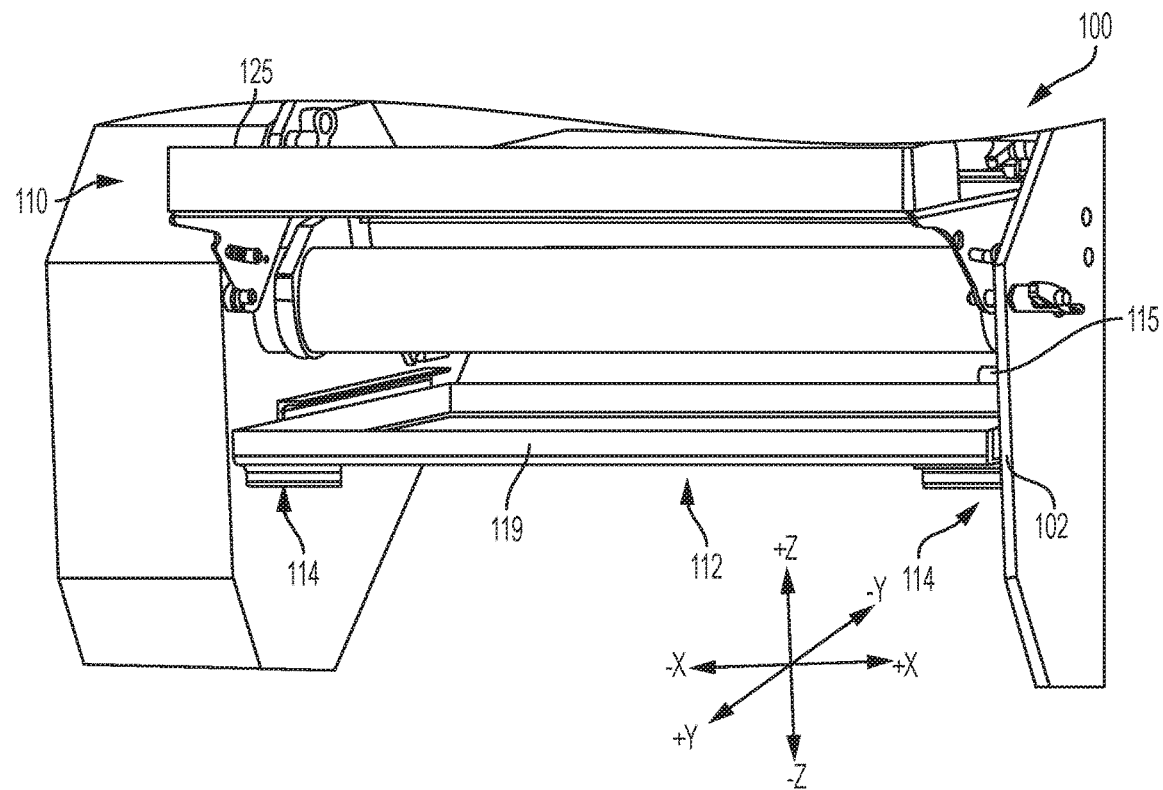
FIG. 7 illustrates a perspective view of the catch tray mounted onto the base frame 102 of the tissue planing assembly of FIG. 2B, according to one or more embodiments shown and described herein.

Referring again to FIG. 2B, the tissue planing assembly 100 further includes the catch tray 112, which is configured to be positioned beneath the blade assembly 130 and configured to catch a portion of the tissue sample as it is processed by the blade assembly 130. The catch tray 112 may be removably positioned beneath the blade assembly 130. Accordingly, the catch tray 112 may be included as one of disassemblable components of the plurality disassemblable components. FIG. 7 illustrates a perspective view of the catch tray 112 mounted onto the base frame 102 beneath the blade assembly 130 so as to be able to catch the portion of a tissue sample that is guided between the shoe 134 and the gripping roller 140 (see FIG. 11B). The catch tray may include a periphery lip 119 extending vertically on all sides of the catch tray to retain the portion of the tissue sample thereon and any fluids that flow down to the catch tray that are used during processing. In the illustrated embodiments, the base frame 102 may define guide rails 114 that the catch tray 112 may longitudinally traverse so as to be guided into position beneath the blade assembly 130. At least one of the guide rails 114 may include a stop 115 at an end of the guide rails 114 configured to indicate that the catch tray 112 has reached the longitudinal end of the guide rails. In some embodiments, the catch tray 112 may be electro-polished or provided with a similar high durability and mirrored surface treatment such that the catch tray 112 may be easily cleaned and sterilized. Alternatively, or in addition to such treatment, the catch tray 112 may be made from a material capable of repeated washing and sterilization (e.g., stainless steel).

Figure 8:
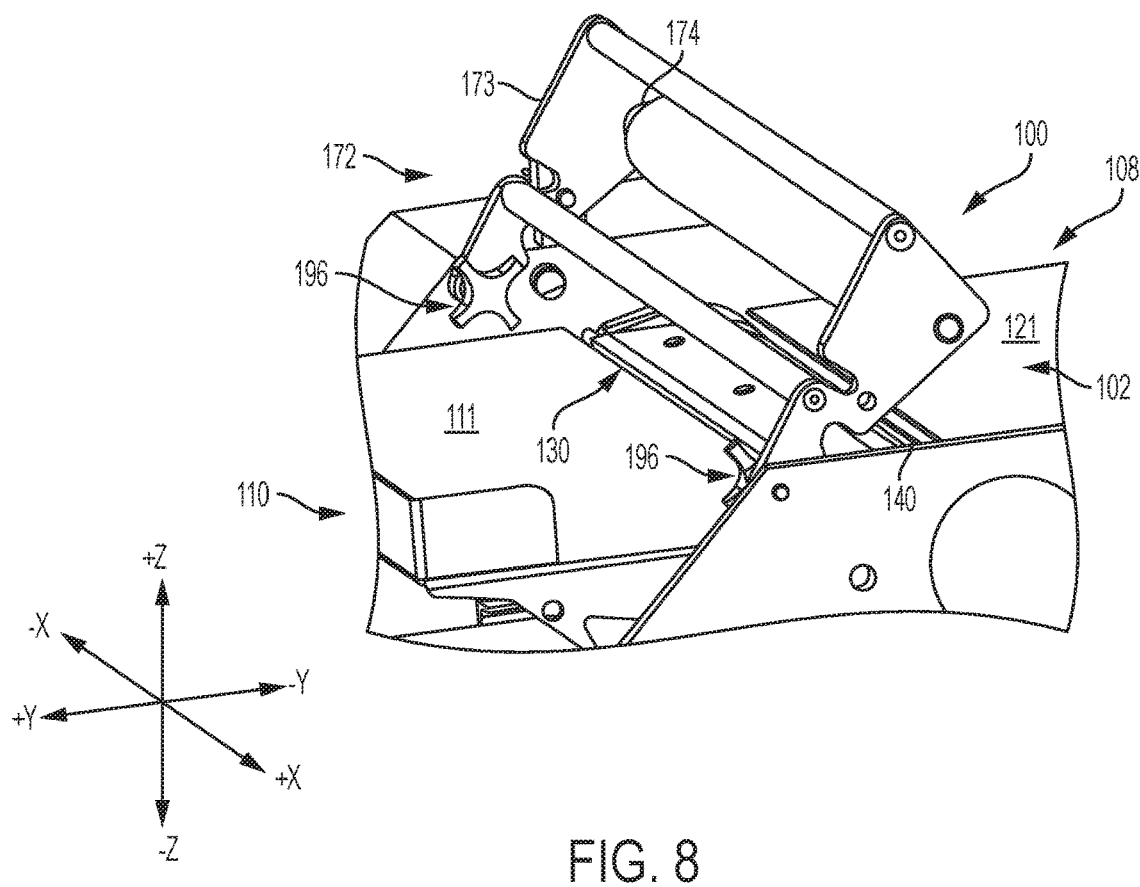
FIG. 8 depicts a perspective view of the hold down roller connected to a base frame of the tissue planing assembly of FIG. 2A, according to one or more embodiments shown and described herein.

Referring again to FIGS. 2A and 2B, rotatably mounted to the base frame 102 may be a hold down roller 172. Referring to FIG. 8, a perspective view of the hold down roller 172 removably coupled to the base frame 102 is depicted. The hold down roller 172 may include a roller frame 173 and a roller 174 rotably coupled to the frame. The hold down roller 172 as a unit may rotate toward the sample conveyor 120 to hold a tissue sample in contact with the sample conveyor 120 while still allowing the sample to move through the cutting assembly. The hold down roller 172 may be removably coupled to the base frame 102 using, for example, spring pins 196 to lock the roller frame 173 of the hold down roller 172 to the base frame 102. In some embodiments, the hold down roller 172 may be one of the disassemblable components of the plurality of disassemblable components. The hold down roller may be made from any materials capable of repeated cleaning and sterilization.

Referring again to FIGS. 2A and 2B, as noted hereinabove, the tissue planing assembly 100 may include a control unit 150. The control unit 150 may be communicatively coupled to the sample conveyor 120 and can execute logic to selectively operate the sample conveyor 120 so as to convey a tissue sample toward the blade assembly 130 to perform a tissue planing operation. The control unit 150 may be housed within the control unit housing 151 that is connected to the base frame 102 by an arm 153, which may be adjustable (e.g., a stainless steel swivel arm).

Figure 9:
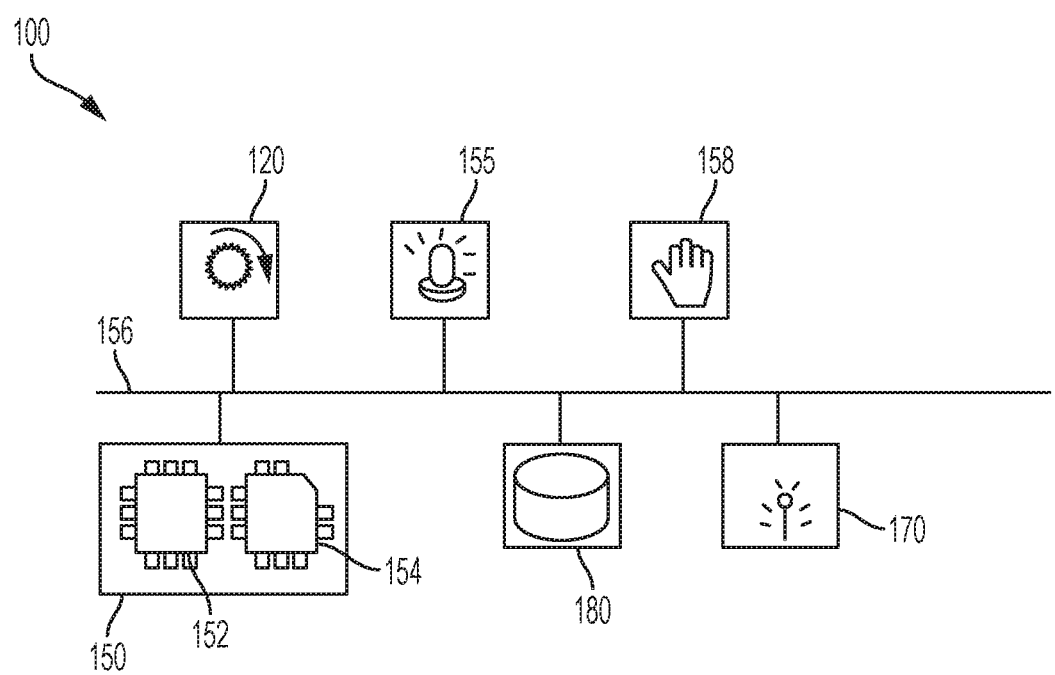
FIG. 9 depicts a schematic diagram of the tissue planing assembly of FIG. 2A, according to one or more embodiments shown and described herein.

FIG. 9 depicts a schematic diagram illustrating communication between the control unit 150 and the sample conveyor 120, the status indicator 155, the user input module 158 and the one or more component sensors 170. The control unit 150 can be any type of computing device and includes one or more processors 152 and one or more memory modules 154. The one or more processors 152 may include any device capable of executing machine-readable instructions stored on a non-transitory computer-readable medium, such as those stored on the one or more memory modules 154. Accordingly, each of the one or more processors 152 may include a controller, an integrated circuit, a microchip, a computer, and/or any other computing device.

The one or more memory modules 154 are communicatively coupled to the one or more processors 152. The one or more memory modules 154 may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the electronic control unit 150, as shown, and/or external to the electronic control unit 150. The one or more memory modules 154 may be configured to store logic (i.e., machine readable instructions) that, when executed by the one or more processors 152, cause the control unit 150 to selectively control operation of the sample conveyor 120.

As noted above, the control unit 150 is communicatively coupled to the various electrical components of the tissue planing assembly 100 over a communication path 156. The communication path 156 may be formed from any medium that is capable of transmitting a signal such as, for example, conductive wires, conductive traces, optical waveguides, or the like. Moreover, the communication path 156 may be formed from a combination of mediums capable of transmitting signals. In some embodiments, the communication path 156 includes a combination of conductive traces, conductive wires, connectors, and buses that cooperate to permit the transmission of electrical data signals between the various components of the components such as processors, memories, sensors, input devices, output devices, and communication devices. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

As noted above, the control unit 150 is communicatively coupled to the sample conveyor 120. For example, the control unit 150 may be communicatively coupled to a motor of the sample conveyor 120 which is configured to rotatively drive the gripping roller 140 described above. The one or more processors 152 of the control unit 150 can execute logic stored on the one or more memory modules 154 to cause the control unit 150 to operate or prevent operation of the sample conveyor 120. Conditions of operation will be discussed more fully below.

As noted above, the tissue planing assembly 100 may include one or more component sensors 170 communicatively coupled to the control unit 150 over the communication path 156. In embodiments, the one or more component sensors 170 are configured to output a signal indicative of at least one of the plurality of disassemblable components missing from the ready configuration. That is when one or more of the disassemblable components are not appropriately mounted on to the base frame 102 of the tissue planing assembly 100, the one or more component sensors 170 output a signal indicating that at least one of the disassemblable components is missing or is not properly mounted on to the base frame 102. For example, the one or more component sensors 170 may include magnetic sensors (e.g., magnet in-position switches). The one or more component sensors 170 may be positioned on the base frame 102 so as to detect the presence and/or absence of the plurality of disassemblable components, as generally indicated in FIG. 2A. Each of the one or more disassemblable components may include one or more dedicated component sensors 170 for detecting the individual disassemblable component. As noted herein, when the signal indicating that at least one of the disassemblable components of the plurality of disassemblable components are missing from the ready configuration, the one or more processors 152 can execute logic to prohibit operation of the sample conveyor 120 and prevent a tissue planing operation from being performed. Accordingly, the tissue planing assembly 100 may only be operational when completely assembled in the ready configuration.

Communicatively coupled to the control unit 150 over the communication path 156 is a user input module 158. The user input module 158 may include tactile input hardware (e.g., knob, lever, button, etc.) that allows an operator to input commands into the control unit 150 to operate the sample conveyor 120 to perform a tissue planing operation on a tissue sample 10. Referring to FIGS. 2A and 2B that user input module 158 may be mounted onto the control unit housing 151 at a position away from the blade assembly 130. The user input module 158 may include a first hand control 157 and a second hand control 159 coupled to the control unit housing 151. In such embodiments, the first hand control 157 and the second hand control 159 are communicatively coupled to the control unit 150 such that when the first hand control 157 and the second hand control 159 are activated, the one or more processors 152 of the control unit 150 (illustrated in FIG. 9) execute logic stored on the one or more memory modules 154 to activate the sample conveyor 120. The first hand control 157 and the second hand control 159 may be biased to an unactivated position, such that continuous and concurrent manipulation of the first and second hand controls 157, 159 to an activated position is needed throughout processing. Accordingly, an operator's hands must remain engaged with the first and second hand controls 157, 159 throughout a tissue planing operation. Stated another way, if at least one of the first hand control 157 and the second hand control 159 is in a deactivated position, the control unit 150 may cause the sample conveyor 120 to stop its conveying movement.

Referring again to FIG. 9, in some embodiments, the tissue planing assembly 100 includes a status indicator 155 communicatively coupled to the control unit 150 that is configured to indicate an operating status of the tissue planing assembly 100. For example, and as shown in FIG. 2A, the status indicator 155 may include a light mounted on the control unit housing 151. The light may change color based on the operating status of the tissue planing assembly 100. For example, when it is determined by the control unit 150 that one or more of the disassemblable components are missing from the ready configuration based on the signal from the one or more component sensors 170, the control unit 150 may cause the light to glow red to indicate that the tissue planing assembly 100 is not ready to perform a tissue planing operation (i.e., a not ready signal). If however, it is determined by the control unit 150 that the plurality of disassemblable components are mounted in the ready configuration, based on the signal from the one or more component sensors 170, the control unit 150 may cause the light to glow blue to indicate that the tissue planing assembly 100 is ready to perform a tissue planing operation (i.e., a ready signal). When the first hand control 157 and the second hand control 159 are activated and the tissue planing assembly 100 is ready to perform a tissue planing operation, the control unit 150 may cause the light to glow green to indicate that the tissue planing assembly 100 is performing a tissue planning operation (i.e., a running signal).

Referring again to FIG. 9, in some embodiments, the tissue planing assembly 100 may include an emergency stop 180 communicatively coupled to the control unit 150 that, when activated outputs a signal that causes the control unit 150 to immediately stop the tissue planing operation. In some embodiments the emergency stop 180 includes tactile input hardware such as a button that can quickly and easily be depressed by a user. Referring to FIG. 2A, the emergency stop 180 may be mounted to the housing 151 of the control unit 150 in proximity to the user input module 158.

Figure 10:
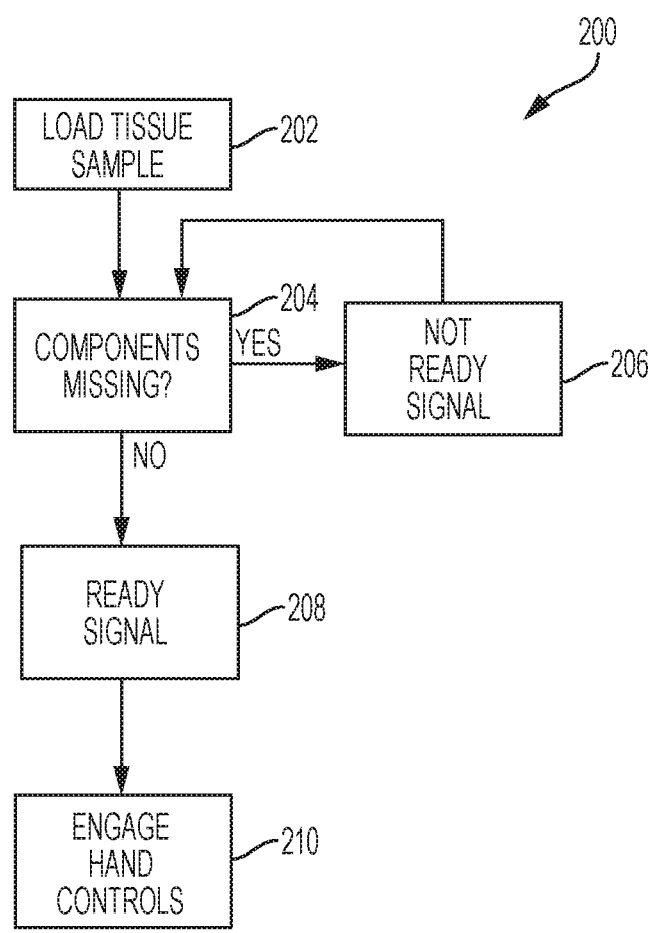
FIG. 10 illustrates a flow diagram representing an exemplary method of processing a tissue sample with the tissue planing assembly of FIG. 2A, according to one or more embodiments shown and described herein.

FIG. 10 illustrates a flow diagram 200 representing an exemplary method of processing a tissue sample with the tissue planing assembly 100 as described herein. Though the various steps of the method are illustrated as having a discrete number in a particular order, a greater or fewer number of steps in various orders may be used without departing from the scope of the present disclosure. With concurrent reference to FIG. 11A, to process a tissue sample 10 with the tissue planing assembly 100, the tissue sample 10 having a epidermis layer 12 and a dermis layer 14 is placed epidermis side down on the front tray 108 of the tissue planing assembly 100 (step 202). In some embodiments, the front tray 108 and/or the tissue sample 10 may be wetted with saline to reduce the coefficient of friction between the surface of the front tray 108 and the tissue sample 10. Accordingly, potential unwanted stretching from sticking to the front tray 108 and resultant rebound of the tissue sample 10 after planing may be reduced.

During step 202, a portion of the tissue sample 10 may be contacted to the sample conveyer such that during operation the sample conveyor 120 will be able to convey the tissue sample 10 without further adjustment of the tissue sample 10 on to the sample conveyor 120. In embodiments including a hold down bar, the hold down bar can be rotated so as to apply a downward pressure to a leading edge of the tissue sample 10 to facilitate initiation of the tissue planing operation and to maintain consistent and constant pressure on the tissue sample 10 as it is processed.

It is noted that in some embodiments, the tissue sample 10 may include an adipose layer 16, such as shown in FIG. 1, that is larger than or equal to 25.4 mm. Through experimentation, it was found that adipose layers of larger than or equal to 25.4 mm may aid in maintaining the integrity of the tissue sample 10 throughout processing. That is instances of tearing of the tissue sample 10 were reduced as compared to tissue samples having thinner adipose layers. For tissue samples with an adipose layer 16 of less than 25.4 mm, a surrogate adipose layer may be positioned on top of the tissue sample 10 in between the tissue sample 10 and the hold down roller 172. For example a sheet of semi rigid polystyrene foam having a thickness of about 25.4 mm (1 inch) may be used as a surrogate adipose layer. In some embodiments, a plastic mesh may be placed on top of the adipose layer 16 between the tissue sample 10 and the hold down roller 172 to further aid in transportation of the tissue sample 10 over the blade assembly 130.

Referring again to FIG. 10, at step 204 the control unit 150 may, based on the signal of the one or more component sensors 170, determine whether one or more disassemblable components of the tissue planing assembly 100 are assembled to the base frame 102 of the tissue planing assembly 100 in a ready configuration. If it is determined that one of the one or more disassemblable components is missing or is not properly assembled to the base frame 102, as shown in FIGS. 2A and 2B, at step 206 the control unit 150 may output a not ready signal with the status indicator 155, described above, indicating that the one or more disassemblable components of the tissue planing assembly 100 are not assembled to the base frame 102 of the tissue planing assembly 100 in the ready configuration. Once properly assembled, as determined by the control unit 150 based on the signal of the one or more component sensors 170, at step 208 the control unit 150 can output a ready signal with the status indictor as described above indicating that the one or more disassemblable components are assembled to the base frame 102 of the tissue planing assembly 100 in the ready configuration and that the tissue planing assembly 100 is, accordingly, ready to perform a tissue planing operation. With the tissue planing assembly 100 properly assembled, at step 210 an operator may concurrently and/or continuously engage the first hand control 157 and the second hand control 159 to cause the control unit 150 to operate the sample conveyor 120 to convey the tissue sample 10 through the blade assembly 130 of the tissue planing assembly 100.

Referring to FIG. 11B, as the tissue sample 10 is introduced to the blade assembly 130 a portion of the tissue sample 10 comprising the epidermis and a portion of the dermis is directed downward between the shoe 134 and the gripping roll to be caught in the catch pan. This portion may be thin enough (e.g., less than or equal to about 0.65 mm) to use as a skin graft, for example, for burn victims or the like. A second portion of the tissue sample 10 is directed above the blade assembly 130 to the rear tray 110. This portion may include the dermis and any adipose tissue that was connected to the dermis. In some embodiments, the remainder dermis and adipose layer may be re-run through the blade assembly to retrieve a dermis only product. Such dermis product may have a thickness of about 1.0 mm to about 5 mm.

Between uses or between processing tissue from different donors, the tissue planing assembly 100 may be disassembled, cleaned, sterilized, and reassembled for future use. Set up and breakdown may take about 15 minutes or less for each operation.

It should now be understood that embodiments described herein are directed to tissue planing assemblies and methods. In particular, tissue planing assemblies as described herein are capable processing tissue samples epidermis side down resulting in larger skin graft products. Moreover, embodiments described herein include easily disassemblable components which allow for easy disassembly, sterilization, and reassembly. Embodiments described herein also include prevention of operation when the tissue planing is not properly assembled or operated which may improve yield and reduce incidents related to improper assembly.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A tissue planing assembly comprising:
   a base frame;
   a plurality of disassemblable components assembled to the base frame and having a ready configuration, wherein the plurality of disassemblable components is configured to support a tissue sample;
   a sample conveyor;
   a blade assembly configured to be coupled to the base frame, wherein the sample conveyor is configured to convey the tissue sample through the blade assembly;
   a control unit communicatively coupled to the sample conveyor; and
   one or more component sensors communicatively coupled to the control unit, the one or more component sensors configured to output a signal indicative of at least one of the plurality of disassemblable components missing from the ready configuration, wherein the control unit prohibits operation of the sample conveyor when at least one of the plurality of disassemblable components is missing from the ready configuration.

2. The tissue planing assembly of claim 1, wherein the plurality of disassemblable components comprises a front tray, wherein the sample conveyor is configured to pull the tissue sample from the front tray and through the blade assembly.

3. The tissue planing assembly of claim 2, wherein the front tray comprises a receiver slot configured to receive a pin of the base frame.

4. The tissue planing assembly of claim 1, wherein the plurality of disassemblable components comprises a rear tray configured to be positioned at a distal end of the blade assembly and configured to receive a portion of the tissue sample as the tissue sample is conveyed through the blade assembly by the sample conveyor.

5. The tissue planing assembly of claim 4, wherein the rear tray is oriented such that a tissue support surface of the rear tray is set at an angle with respect to a front tray.

6. The tissue planing assembly of claim 5, wherein the rear tray is rotatably adjustable about an axis to adjust the angle of the rear tray.

7. The tissue planing assembly of claim 4, wherein the rear tray is lockable in the ready configuration.

8. The tissue planing assembly of claim 1, wherein the plurality of disassemblable components comprises a catch tray configured to be positioned beneath the blade assembly and configured to catch a portion of the tissue sample as it is processed by the blade assembly.

9. The tissue planing assembly of claim 1, further comprising a rotatable hold down bar coupled to the base frame and configured to hold down the tissue sample as the sample conveyor conveys the tissue sample through the blade assembly.

10. The tissue planing assembly of claim 1, further comprising a status indicator communicatively coupled to the control unit, wherein the status indicator is configured to produce a signal indicative of an operating status of the tissue planing assembly, wherein the operating status includes a ready signal, wherein each of the plurality of disassemblable components are positioned within the ready configuration, a not ready signal, wherein at least one of the plurality of disassemblable components is not positioned within the ready configuration, and a running signal, wherein the tissue planing assembly is operating.

11. A tissue planing assembly comprising:
a base frame;
a sample conveyor coupled to the base frame;
a blade assembly coupled to the base frame, wherein the sample conveyor is configured to convey a tissue sample through the blade assembly;
a control unit communicatively coupled to the sample conveyor; and
a first hand control and a second hand control communicatively coupled to the control unit, wherein the control unit executes logic to operate the sample conveyor only when both the first hand control and the second hand control are activated.

12. The tissue planing assembly of claim 11, further comprising a control unit housing, wherein the control unit housing is pivotally coupled to the base frame.

13. The tissue planing assembly of claim 12, wherein the first hand control and the second hand control are coupled to the control unit housing.

14. The tissue planing assembly of claim 11, further comprising a catch tray removably positioned beneath the blade assembly and configured to catch a portion of the tissue sample as it is processed by the blade assembly.

15. The tissue planing assembly of claim 14, further comprising one or more component sensors communicatively coupled to the control unit, the one or more component sensors configured to output a signal indicative of the catch tray missing from a ready configuration, wherein the tissue planing assembly is only operable when the catch tray is positioned within the ready configuration.

16. The tissue planing assembly of claim 11, further comprising:
one or more trays removably couplable to the base frame; and
one or more component sensors communicatively coupled to the control unit, the one or more component sensors configured to output a signal indicative of one or more of the one or more trays missing from a ready configuration, wherein the tissue planing assembly is only operable when each of the one or more trays are positioned within the ready configuration.

17. A tissue planing assembly comprising:
a base frame;
a sample conveyor coupled to the base frame; and
a blade assembly coupled to the base frame, wherein the sample conveyor is configured to convey a tissue sample through the blade assembly, the blade assembly comprising:
a shoe defining a groove;
a blade positioned on a top surface of the shoe proximate to the groove;
a blade clamp configured to rigidly clamp the blade to the shoe; and
one or more spacers positionable within the groove adjacent to the blade to adjust a cutting depth of the blade.

18. The tissue planing assembly of claim 17, wherein the sample conveyor comprises a gripping roller positioned relative to a cutting edge of the blade, wherein a position of the cutting edge of the blade is adjustable relative to the gripping roller.

19. This tissue planing assembly of claim 17, wherein the one or more spacers are positionable within the groove behind the blade in a longitudinal direction.

20. The tissue planing assembly of claim 17, wherein each of the one or more spacers correspond to a resulting skin graft thickness.

* * * * *